United States Patent [19]

Iwasaki et al.

[11] Patent Number: 4,762,547

[45] Date of Patent: Aug. 9, 1988

[54] ENHANCEMENT OF BIOCIDE

[75] Inventors: Tetsuji Iwasaki, Wakayama; Yuichi Hioki, Wakayama, both of Japan

[73] Assignee: Kao Corporation, Tokyo, Japan

[21] Appl. No.: 815,837

[22] Filed: Jan. 3, 1986

[30] Foreign Application Priority Data

Jan. 18, 1985 [JP] Japan .................................. 60-7147

[51] Int. Cl.$^4$ ..................... A01N 57/00; A01N 63/00; A61K 37/54
[52] U.S. Cl. .......................................... 71/65; 71/69; 71/70; 71/71; 71/79; 71/80; 71/86; 71/87; 71/97; 71/119; 424/94.6; 514/143; 514/493; 514/596
[58] Field of Search .................... 424/94.6; 71/65, 69, 71/70, 71, 79, 80, 86, 87, 97, 119

[56] References Cited

U.S. PATENT DOCUMENTS

| 3,070,497 | 12/1962 | Knight | 424/94.6 |
| 3,081,225 | 3/1963 | Farnham et al. | 424/94.6 |
| 3,493,652 | 2/1970 | Hartman | 424/94.6 |
| 3,721,733 | 3/1973 | Leeuwen | 424/94.6 |

*Primary Examiner*—Sam Rosen
*Attorney, Agent, or Firm*—Flynn, Thiel, Boutell & Tanis

[57] ABSTRACT

A biocide is enhanced in the effect by applying an esterase to a plant stem, leaves or an insect in advance to or together with the application of the biocide. The esterase decomposes the waxy outer layers of plants and insects.

10 Claims, No Drawings

ENHANCEMENT OF BIOCIDE

The invention relates to a biocidal method and a biocide composition. The invention improves a conventional biocide in the biological effect by applying it together with an enhancing agent such as a specified enzyme.

STATEMENT OF PRIOR ART

A synergist which serves to enhance the biological effect of biocides and which is also called the adjuvant consists chiefly of surface active agents. It is used together with agricultural/horticultural biocides whose effect is exhibited by application to, especially, plant stems and leaves, e.g., herbicides, bacteriocides, insecticides or miticides. Agricultural/horticultural biocides would more or less cause environmental pollution to occur as they are often used. When they are used together with a surface active agent which is relatively harmless to environments, however, they can be reduced in quantity and frequency of their use and be improved with their biological effect retained. Nevertheless, the surface active agents used chiefly as the synergist must be selected carefully in respect of their kind and concentration, because they are in some cases apt to invite drug-induced sufferings.

SUMMARY OF THE INVENTION

The present inventors have earnestly studied how to make up for the defects in the conventional synergists and have finally attained the present invention based on the finding that an esterase incorporated in an agricultural/horticultural biocide can exhibit an excellent biological effect enhancing activity on weeds, bacilli and insects irrespective of their kind.

This invention thus provides a biocidal method which comprises applying a biocide to plant stems and leaves or insects, characterized in that an esterase is applied to the plant stems and leaves or insects prior to or together with the application of the biocide, and a synergist for biocides, characterized by containing an esterase.

The invention further provides a method for enhancing a biocide, which comprises the step of applying an esterase to a plant stem, leaves or an insect in advance to or together with the application of said biocide. The invention moreover relates to a biocide composition which comprises a biocide and an esterase.

The esterase used in this invention includes lipase and cutinase. The lipase is one originating in animals, vegetables or microorganisms, preferably one originating in microorganisms from the viewpoint of price and activity. For example, lipase sources include those originating in the genera Candida, Pseudomonas, Rhizopus, Aspergillus and Mucor. Those originating in the genus Pseudomonas are the most preferable. Commercially available products thereof can be used for the present purpose. Cutinase sources preferably include those originating in plant bacilli.

In the practice of this invention, the esterase can be applied to plant stems and leaves or insects prior to the application of the biocide by spraying an aqueous solution of the esterase over them before the application of the biocide. The concentration of the aqueous esterase solution should be at least 0.1 ppm, preferably at least 1 ppm. The time for the subsequent spraying of the biocide need not be specified, and may be decided properly depending on the concentration of the aqueous esterase solution and whether or not the enzyme is deactivated by the biocide. For safety, however, a lapse of at least six hours is generally required for the subsequent spraying.

When the esterase is one which will not be deactivated by a biocide, it is possible to spray the biocide immediately after the aqueous esterase solution has been sprayed, or otherwise it is also possible to spray them together in the form of a composition containing the esterase and the biocide.

The biocides used in this invention nclude pyrethroid insecticides such as Fenvalerate (α-cyano-3-phenoxybenzyl 2-(4-chlorophenyl)-3-methylvalerate) and Baythroid (cyano(4-fluoro-3-phenoxyphenyl)methyl 3-(2,2-dichloroethenyl)-2,2-dimethylcyclopropanecarboxylate); organophosphorus insecticides such as DDVP (2,2-dichlorovinyl dimethyl phosphate), Sumithion (dimethyl 4-nitro-m-tolyl phosphorothionate), Marathon (S-[1,2-bis(ethoxycarbonyl)ethyl]dimethyl phosphorothiolthionate), Dimethoate (dimethyl S-(N-methylcarbamoylmethyl) phosphorothiolthionate), Elsan (S-[α-(ethoxycarbonyl)benzyl]dimethyl phosphorothiolthionate) and Baycid (O,O-dimethyl O-(3-methyl-4-methylmercaptophenyl)thiophosphate); carbamate insecticides such as Bassa (o-butylphenyl methylcarbamate), MTMC (m-tolyl methylcarbamate), Meobal (3,4-dimethylphenyl N-methylcarbamate) and NAC (1-naphthyl N-methylcarbamate); and other insecticides such as Methomyl (methyl-N-[(methylcarbamoyl)oxy]thioacetimide) and cartap (1,3-bis(carbamoylthio)-2-(N,N-dimethylamino)propane hydrochloride).

Miticides include, for example, Sumite (2-(p-tert-butylphenoxy)isopropyl 2-chloroethyl sulfide), Acricid (2,4-dinitro-6-se-butylphenyl dimethylacrylate), Chlormite (isopropyl 4,4-dichlorobenzilate), Akar (ethyl 4,4-dichlorobenzilate), Kelthane (1,1-bis(p-chlorophenyl)-2,2,2-trichloroethanol), Citrazon (ethyl O-benzoyl-3-chloro-2,6-dimethoxybenzohydroxamate), Plictran (tricyclohexyltin hydroxide), and Omite (2-(p-tert-butylphenoxy)cyclohexyl 2-propinyl sulfite).

Bactericides include, for example, organophosphorus bacteriocides such as Dithane (zinc ethylenebisdithiocarbamate), Manneb (manganese ethylenebisdithiocarbamate) and Thiram (bis(dimethylthiocarbamoyl)disulfide), and other bactericides such as Benlate (methyl 1-(butylcarbamoyl)-2-benzimidazolecarbamate), Difolatan (N-tetrachloroethylthio-4-cyclohexane-1,2-dicarboxyimide), Daconol (tetrachloroisophthalonitrile), Pansoil (5-ethoxy-3-trichloromethyl-1,2,4-thiadiazole), Thiophanate-methyl (1,2-bis(3-methoxycarbonyl-2-thioureido)benzene), Rabcide (4,5,6,7-tetrachlorophthalide), Kitazin P (O,O-diisopropyl S-benzyl phosphorothioate), Hinosan (O-ethyl S,S-diphenyl dithiophosphate), Brobenazol (3-allyloxy-1,2-benzothiazole 1,1-dioxide).

Herbicides include, for example, Stam (3,4-dichloropropionanilide), Satan (S-(4-chlorobenzyl) N,N-diethylchiolcarbamate), Lasso (2-chloro-2′,6′-diethyl-N-(methoxymethyl)acetanilide), Glyphosate (N-(phosphonomethyl)glycine isopropylamine salt), DCMU (3-(3,4-dichlorophenyl)-1,1-dimethylurea), and Gramoxon (1,1′-dimethyl-4,4′-dipyridinium dichloride).

Plant growth control agents include, for example, MH (maleic hydrazide) and Ethrel (2-chloroethylphosphonic acid).

The biocide herein need not be specified in its form, which may be an emulsion, a hydrate or a flowable preparation, for instance. It can be used together with a surface active agent which is effective and free of drug-induced sufferings as a synergist, whereby its effect can be enhanced outstandingly.

(Action and Effect)

The reason why the biocidal method of this invention brings about an outstanding biocidal effect may be explained by the following conceivable mechanism.

The outer skin of plants or insects is covered with waxy layers such as esters of higher fatty acids with alcohols, which play a role of protecting their tissues from external physical and chemical stimulation. When a biocide is sprayed, it will penetrate in an amount of no more than by 20 to 30% into the inside tissues of plants or insects. Moreover, the sprayed biocide is apt to be washed away by external changes such as rainfalls and unable to display its own effect.

In this invention, an esterase used as a synergist incorporated in the biocide serves to decompose the foliar wax of plants or the epidermal wax of insects, thereby destroying the wax structure, so that the biocide can penetrate in a larger amount and be prevented from being washed away with external changes such as rainfalls, whereby its biocidal effect can be increased.

EXAMPLES

The biological effect enhancing activity in this invention will now be illustrated by the following examples.

EXAMPLE 1

Powdery lipase (originating in Pseudomonas bacteria) was dissolved in water until its concentration reached 10, 100 and 1,000 ppm, respectively, and each solution was sprayed over livid amaranth weeds (6 cm in height) which had been grown up to a tetrafoliate stage. After 24 hours, a 400-fold diluted solution of an 80% DCMU (Karmex D) hydrate was sprayed over the weeds in such an amount that the effective ingredient be 20 g/are per pot. After 10 days, the weeds grown above the ground were weighed, and the herbicidal power was represented by the percentage of withered weeds against those grown on the non-sprayed zone. The result is shown in Table 1.

TABLE 1

|  |  | Lipase concentration (ppm) | | | |
| --- | --- | --- | --- | --- | --- |
|  |  | 0 | 10 | 100 | 1000 |
| 400-fold diluted solution of 80% DCMU hydrate | 0 | 0 | 0 | 0 | 0 |
|  | 20 g/are (effective ingredient) | 48.5 | 90.7 | 95.7 | 98.0 |

Figures show herbicidal power by percentage.

EXAMPLE 2

Powdery lipase (originating in Pseudomonas bacteria) was dissolved in a concentration of 10, 100 and 1,000 ppm in water. An 80% DCMU hydrate was diluted 400-fold with the above dilute solution. The solution was sprayed over livid amaranth weeds (6 cm in height), which had been grown up to a tetrafoliate stage, in an effective ingredient amount of 20 g/are and 40 g/are. After 10 days, the weeds grown above the ground were weighed, and the herbicidal power was represented by the percentage of withered weeds against those grown on the non-sprayed zone. The result is shown in Table 2.

TABLE 2

|  |  | Lipase concentration (ppm) | | | |
| --- | --- | --- | --- | --- | --- |
|  |  | 0 | 10 | 100 | 1000 |
| 400-fold diluted solution of 80% DCMU hydrate | 0 | 0 | 0 | 0 | 0 |
|  | 20 g/are (effective ingredient) | 48.0 | 91.0 | 95.4 | 98.2 |
|  | 40 g/are (effective ingredient) | 67.9 | 100 | 100 | 100 |

Figures show herbicidal power by percentage.

EXAMPLE 3

Powdery cutinase originating in Colletotrichum bacteria was dissolved in water until its concentration reached 1, 10 and 100 ppm, and a 50% Sumilex hydrate was diluted 1,500-fold with the above dilute solution. The solution was subsequently sprayed over cucumber stems and leaves in a tetrafoliate stage in an amount of 10 ml per pot. Immediately after and 24 hours after the spraying, a suspension of gray mold spores was sprayed for infection, and the rate of extermination was determined Separately, an artificial rainfall (20 mm) was applied to the plants immediately after and 24 hours after the aforesaid spraying of the diluted solution. After the artificial rainfall, a suspension of gray mold spores was sprayed for infection, and the rate of extermination was determined by counting the number of spots occurring on the plant stems and leaves and calculating the percentage of the spots against those occurring on the non-sprayed zone. The result is shown in Table 3.

TABLE 3

|  | Time when spore suspension was sprayed | Cutinase concentration (ppm) | | | |
| --- | --- | --- | --- | --- | --- |
|  |  | 0 | 1 | 10 | 100 |
| No artificial rainfall was applied | Immediately after the solution was sprayed | 81 | 90 | 100 | 100 |
|  | 24 hours after the solution was sprayed | 79 | 92 | 100 | 100 |
| Artificial rainfall applied (20 mm) | Immediately after the solution was sprayed, artificial rainfall was applied, and subsequently spore suspension was sprayed | 48 | 50 | 56 | 60 |
|  | 24 hours after the solution was sprayed, artificial rainfall was applied, and subsequently spore suspension was sprayed | 65 | 82 | 92 | 97 |

Figures show average rate of extermination (%) per 10 pots.

EXAMPLE 4

Powdery lipase (originating in Enterobacterium) was dissolved in water until its concentration reached 1, 10 and 100 ppm, and a 50% Plictran hydrate was diluted 2,000 fold with this enzyme solution. The diluted solution was sprayed over haricot bean plants grown to a hexa- to hepta-foliate stage in an amount of 20 ml per pot. 12 hours after the spraying, 30 female imagos of tetranychus mite were inoculated on each plant. After three days, the surviving mites were counted, and the miticidal rate was determined by comparison with the number of mites surviving on the non-sprayed zone.
The result is shown in Table 4.

TABLE 4

|  |  | Lipase concentration (ppm) | | | |
| --- | --- | --- | --- | --- | --- |
|  |  | 0 | 1 | 10 | 100 |
| 2,000-fold diluted soluton of 50% Plictran hydrate | Sprayed 20 ml/pot | 0 48 | 0 78 | 0 90 | 0 100 |

Figures show miticidal rate (%) in comparison with non-sprayed zone.

EXAMPLE 5

Powdery cutinase (originating in Botrytis bacteria) was dissolved in water until its concentration reached 1, 10 and 100 ppm, and a 40% Sumithion hydrate was diluted 1,000-fold with this solution. The diluted solution was sprayed in an amount of 20 ml over 50 imagos of green rice leaf hopper kept in an insect breeding box. After two days, dead insects were counted, and the insecticidal rate (%) was determined by comparison with the non-sprayed zone. The result is shown in Table 5.

TABLE 5

|  |  | Cutinase concentration (ppm) | | | |
| --- | --- | --- | --- | --- | --- |
|  |  | 0 | 1 | 10 | 100 |
| 1,000-fold diluted solution of 40% Sumithion hydrate | 0 20 ml | 0 64 | 0 90 | 0 95 | 0 100 |

Figures show insecticidal percentage (%) in comparison with non-sprayed zone.

EXAMPLE 6

40 parts by weight of the original body of DCMU, 4 parts by weight of cutinase powder originating in Collectotrichum, 8 parts by weight of diethanol amine salt of a polyoxyethylene-alkyl phosphate and 48 parts by weight of clay were mixed with each other to produce a DCMU hydrate. It was diluted 400 times with water. It was then sprayed in an amount of 20 grams of the effective component per are over amaranth weeds which have grown up to 6 cm height. In 10 days, a weight of the living weeds above the ground was measured. A herbicidal power was calculated in terms of a percent of withered weeds to the non-treated weeds. An 80 percent DCMU, being available with a tradename of Karmex D, was used as a control. Results are shown in Table 6.

TABLE 6

|  | dilution | herbicidal power |
| --- | --- | --- |
| Example 6 (the invention) | x 400 | 90.4 |
| control | x 800 | 37.2 |

EXAMPLE 7

45.5 g of Karmex D, a conventional herbicide, 4,5 g of sodium salt of formalin condensate with naphthalene sulfonic acid, having a condensation degree of 4, 50 g of water and 180 g of glass beads (medeia) were mixed with each other at a volume ratio of glass beads to the dispersion of 50:50. The mixture were ground with a sand grinder having an inner volume of 400 ml, at a disk-peripheral velocity of 6 m/sec, at 20° to 25° C., for 3 hours. By filtration under a pressure, 68 g of fine powder of Karmex D was obtained.

A size distribution of the obtained fine Karmex D (DCMU) is shown in Table 7, showing that 95 wt.% of the powder had a size of not larger than 0.5 micron.

TABLE 7

| particle size | distribution (wt. %) |
| --- | --- |
| larger than 0.5 micron | 5 |
| 0.5 to 0.2 | 84 |
| 0.2 to 0.1 | 10 |
| 0.1 to 0.05 | 1 |
| not larger than 0.05 | 0 |

Powder of lipase enzyme, originating in Pseudomonas bacteria, was dissolved in water at concentrations of 10 and 100 ppm, respectively. Further the DCMU dispersion was diluted with the respective lipase solutions. The obtained dilution liquid was sprayed over livid amaranth weeds which had been grown up to the tetrafoliate stage, having 6 cm height, in an amount of 20 g/are as the effective ingredient. In 10 days, the weeds grown above the ground were weighed and a herbicidal power was calculated in comparison with the non-treated zone. Results are shown in Table 8.

TABLE 8

|  |  | lipase content (ppm) | | |
| --- | --- | --- | --- | --- |
|  |  | 0 | 10 | 100 |
| fine powder of DCMU | 0 10 g/are | 0 69.4 | 0 91.4 | 0 100 |
| DCMU hydrate (20 microns size) | 10 g/are | 30.2 | 62.1 | 87.3 |

The embodiments of the invention in which an exclusive privilege or property is claimed are defined as follows:

1. In a method for controlling a plant, plant pest or an insect by the application of a biocide to the plant, or insect, the improvement comprising: decomposing the the outer waxy layer of the plant or insect by applying an esterase to said plant, or insect in advance of or together with the application of the biocide.

2. A method as claimed in claim 1, in which said esterase is a lipase or cutinase originating in plant bacilli.

3. The method of claim 1, wherein the esterase is applied to the plant, or insect in advance of the application of the biocide.

4. The method of claim 1, wherein the esterase is a lipase derived from Pseudomonas bacteria and the biocide is 3-(3,4-dichlorophenyl)-1,1-dimethylurea.

5. The method of claim 4, wherein the lipase is applied to livid amaranth weeds prior to the application of 3-(3,4-dichlorophenyl)-1,1-dimethylurea.

6. The method of claim 1, wherein the esterase is a lipase derived from Enterobacterium and the biocide is a hydrate of tricyclohexyltin hydroxide.

7. The method of claim 1, wherein the esterase is a cutinase derived from Botrytis bacteria and the biocide is a hydrate of dimethyl 4-nitro-m-tolyl phosphorothionate.

8. A pesticidal process which comprises: spraying an aqueous solution of an esterase onto insects per se, weeds or other plants containing bacteria, mites or insects and also spraying a liquid agricultural chemical biocidal composition onto said weeds, other plants or insects, the amount of said esterase sprayed being an amount effective to increase the biocidal effect of said agricultural chemical biocidal composition and said agricultural chemical biocidal composition being sprayed simultaneously with or after spraying said aqueous solution of said esterase.

9. A process as claimed in claim 8 in which said esterase is lipase or cutinase.

10. A process as claimed in claim 8 in which said agricultural chemical biocidal composition contains an effective biocidal amount of an insecticide, a miticide, a bactericide, an herbicide or a plant growth control agent.

* * * * *